US006546271B1

(12) United States Patent
Reisfeld

(10) Patent No.: US 6,546,271 B1
(45) Date of Patent: Apr. 8, 2003

(54) VASCULAR RECONSTRUCTION

(75) Inventor: Daniel Reisfeld, Haifa (IL)

(73) Assignee: Bioscience, Inc., New Brunswick, NJ (US)

( * ) Notice: Subject to any disclaimer, the term of this patent is extended or adjusted under 35 U.S.C. 154(b) by 0 days.

(21) Appl. No.: 09/411,154

(22) Filed: Oct. 1, 1999

(51) Int. Cl.$^7$ ............................................... A61B 5/05
(52) U.S. Cl. ........................................................ 600/407
(58) Field of Search ................................ 600/407, 462, 600/463, 467, 459, 443, 424; 128/916, 899

(56) References Cited

U.S. PATENT DOCUMENTS

| | | |
|---|---|---|
| 3,316,896 A | 5/1967 | Thomasset |
| 4,157,572 A | 6/1979 | Kennedy et al. ............... 360/33 |
| 4,173,228 A | 11/1979 | Van Steenwyk et al. ..... 128/653 |
| 4,459,990 A | 7/1984 | Barnea ......................... 128/656 |
| 4,522,212 A | 6/1985 | Gelinas et al. ............... 128/642 |
| 4,628,937 A | 12/1986 | Hess et al. ................... 128/642 |
| 4,630,203 A | 12/1986 | Szirtes |
| 4,660,571 A | 4/1987 | Hess et al. ................... 128/784 |
| 4,682,603 A | 7/1987 | Franz .......................... 128/642 |
| 4,697,595 A | 10/1987 | Breyer et al. ................. 128/660 |
| 4,699,147 A | 10/1987 | Chilson et al. ............... 128/642 |
| 4,821,731 A * | 4/1989 | Martinelli et al. ...... 128/662.06 |
| 4,875,165 A | 10/1989 | Fencil et al. |
| 4,878,115 A | 10/1989 | Elion .......................... 358/111 |
| 4,892,104 A | 1/1990 | Ito et al. ...................... 128/697 |
| 4,898,181 A | 2/1990 | Kessier ........................ 128/699 |
| 4,905,705 A | 3/1990 | Kizakevich et al. .......... 128/69 |

(List continued on next page.)

FOREIGN PATENT DOCUMENTS

| | | |
|---|---|---|
| EP | 501993 | 6/1997 |
| EP | 974936 | 1/2000 |
| WO | WO 94/04938 | 3/1994 |
| WO | WO 96/05768 | 2/1996 |
| WO | WO 97/24983 | 6/1997 |
| WO | WO 98/12663 | 3/1998 |
| WO | WO 98/35720 A2 | 8/1998 |
| WO | WO 98/35720 A3 | 8/1998 |
| WO | WO 99/05971 | 2/1999 |

OTHER PUBLICATIONS

Castleman, K.R.; Digital Image Processing (1996); "Curve and Surface Fitting"; pp. 501–507.

Jain, A.K.; Fundamentals of Digital Image Processing (1989); "The Back–Projection Operator"; pp. 445.

(List continued on next page.)

*Primary Examiner*—Marvin M. Lateef
*Assistant Examiner*—Eleni Mantis Mercader
(74) *Attorney, Agent, or Firm*—Frederick L. Herman; Louis J. Capezzuto

(57) ABSTRACT

A method for vascular reconstruction comprises the steps of advancing a catheter having a position sensor into the vessel, acquiring position information from the sensor at a plurality of points in the vessel, calculating a center-line of the vessel based on said position information, and calculating the inner surface of the vessel. The method of the invention preferably further comprises displaying the vessel reconstruction. The invention is also directed to apparatus for reconstructing vessels which comprises a catheter having a position sensor contained therein, means for acquiring position information from said sensor at a plurality of points in said vessel, means for calculating a centerline of the vessel based on said position information, and means for calculating the inner surface of the vessel.

26 Claims, 9 Drawing Sheets

U.S. PATENT DOCUMENTS

| | | | | |
|---|---|---|---|---|
| 4,911,174 | A | 3/1990 | Pederson et al. | 128/695 |
| 4,922,912 | A | 5/1990 | Watanabe | 128/642 |
| 4,940,064 | A | 7/1990 | Desai | 128/784 |
| 4,955,382 | A | 9/1990 | Franz et al. | 128/642 |
| 4,962,767 | A | 10/1990 | Brownlee | 128/786 |
| 4,979,510 | A | 12/1990 | Franz et al. | 128/642 |
| 5,022,396 | A | 6/1991 | Watanabe | 128/642 |
| 5,038,791 | A | 8/1991 | Collins et al. | 128/696 |
| 5,042,486 | A | 8/1991 | Pfeiler et al. | 128/653 |
| 5,056,524 | A | 10/1991 | Oe | 128/654 |
| 5,127,403 | A | 7/1992 | Brownlee | 128/419 P |
| 5,146,926 | A | 9/1992 | Cohen | 128/710 |
| 5,156,151 | A | 10/1992 | Imran | 128/642 |
| 5,175,773 | A | 12/1992 | Garreau et al. | |
| 5,215,103 | A | 6/1993 | Desai | 128/784 |
| 5,227,969 | A | 7/1993 | Waggener et al. | |
| 5,228,442 | A | 7/1993 | Imran | 128/642 |
| 5,231,995 | A | 8/1993 | Desai | 128/784 |
| 5,239,999 | A | 8/1993 | Imran | 128/642 |
| 5,243,981 | A | 9/1993 | Hudrlik | 607/11 |
| 5,255,678 | A | 10/1993 | Deslauriers et al. | 128/642 |
| 5,255,679 | A | 10/1993 | Imran | 128/642 |
| 5,279,299 | A | 1/1994 | Imran | 128/642 |
| 5,293,869 | A | 3/1994 | Edwards et al. | 128/642 |
| 5,297,549 | A | 3/1994 | Beatty et al. | 128/642 |
| 5,311,866 | A | 5/1994 | Kagan et al. | 128/642 |
| 5,313,943 | A | 5/1994 | Houser et al. | 128/642 |
| 5,324,284 | A | 6/1994 | Imran | 606/15 |
| 5,341,807 | A | 8/1994 | Nardella | 128/642 |
| 5,345,936 | A | 9/1994 | Pomeranz et al. | 138/642 |
| 5,383,917 | A | 1/1995 | Desai et al. | 607/702 |
| 5,391,199 | A | 2/1995 | Ben-Haim | 607/122 |
| 5,409,000 | A | 4/1995 | Imran | 128/642 |
| 5,433,198 | A | 7/1995 | Desai | 128/642 |
| 5,443,489 | A | 8/1995 | Ben-Haim | 607/115 |
| 5,454,370 | A | 10/1995 | Avitall | 128/642 |
| 5,458,116 | A | 10/1995 | Egler | 128/710 |
| 5,485,849 | A | 1/1996 | Panescu et al. | 128/699 |
| 5,487,391 | A | 1/1996 | Panescu | 128/699 |
| 5,531,227 | A | 7/1996 | Schneider | |
| 5,546,951 | A | 8/1996 | Ben-Haim | 128/702 |
| 5,549,109 | A | 8/1996 | Samson et al. | 128/642 |
| 5,558,191 | A | 9/1996 | Lai | 188/379 |
| 5,588,432 | A | 12/1996 | Crowley | 128/660.03 |
| 5,595,183 | A | 1/1997 | Swanson et al. | 128/697 |
| 5,637,090 | A | 6/1997 | McGee et al. | 604/95 |
| 5,640,967 | A | 6/1997 | Fine et al. | 128/710 |
| 5,657,755 | A | 8/1997 | Desai | 128/642 |
| 5,687,737 | A | 11/1997 | Branham et al. | 128/710 |
| 5,697,377 | A | 12/1997 | Wittkampf | 128/696 |
| 5,718,241 | A | 2/1998 | Ben-Haim et al. | 128/702 |
| 5,729,129 | A | 3/1998 | Acker | 324/207.12 |
| 5,730,704 | A | 3/1998 | Avitall | 600/374 |
| 5,738,096 | A | 4/1998 | Ben-Haim | 128/653.1 |
| 5,752,513 | A | 5/1998 | Acker et al. | 128/653.1 |
| 5,755,664 | A | 5/1998 | Rubenstein | 600/377 |
| 5,771,895 | A | * 6/1998 | Slager | 128/662.06 |
| 5,782,773 | A | 7/1998 | Kuo et al. | 600/523 |
| 5,797,849 | A | 8/1998 | Vesely et al. | |
| 5,803,084 | A | 9/1998 | Olson | 128/699 |
| 5,820,568 | A | 10/1998 | Willis | 600/523 |
| 5,830,145 | A | * 11/1998 | Tenhoff | 600/463 |
| 5,830,150 | A | 11/1998 | Palmer et al. | 600/523 |
| 5,840,031 | A | 11/1998 | Crowley | 600/440 |
| 5,842,984 | A | 12/1998 | Avitall | 600/374 |
| 5,879,305 | A | * 3/1999 | Yock et al. | 600/462 |
| 5,889,524 | A | 3/1999 | Sheehan et al. | 345/419 |
| 5,913,820 | A | * 6/1999 | Bladen et al. | 600/407 |
| 5,921,924 | A | 7/1999 | Avitall | 600/374 |
| 5,931,835 | A | 8/1999 | Mackey | 606/34 |
| 5,931,863 | A | 8/1999 | Griffin, III et al. | 607/122 |
| 5,951,485 | A | 9/1999 | Cyrus et al. | 600/523 |
| 5,954,665 | A | 9/1999 | Ben-Haim | 600/515 |
| 5,999,587 | A | 12/1999 | Ning et al. | |
| 6,047,080 | A | 4/2000 | Chen et al. | |
| 6,052,618 | A | 4/2000 | Dahlke et al. | |
| 6,066,094 | A | 5/2000 | Ben-Haim | |
| 6,083,162 | A | * 7/2000 | Vining | 600/407 |

OTHER PUBLICATIONS

Foley J.D., van Dam A., Feiner S.K., Hughes J.F.; 2nd Edition in C Computer Graphics Principles and Practice (1996); "Filling Algorithms"; pp. 979–986.

Gerstenfeld E., Sahakin A., Swiryn S.; Evidence for Transient Linking of Atrial Excitation During Atrial Fibrillation in Humans (1992); Circulation vol. 86, No. 2, pp 375–382.

Gerstenfeld E., Sahakian A., Baerman J., Ropella K., Swiryn S.; Detection of Changes in Atrial Endocardial Activation With Use of an Orthogonal Catheter (1991); JACC vol. 18, No. 4, pp 1034–1042.

Kadish A., Spear J., Levine J., Hanich R., Prood C., Moore E.; Vector Mapping of Myocardial Activation (1986); Laboratory Investigation Arrhythmia vol. 74, No. 3, pp 603–615.

Kass et al.; Proceedings of First International Conference Vision (1987); Snakes: Active Contour Models; pp 259–268.

Terzopoulos D.; Transactions on Pattern Analysis and Machine Intelligence (1986), vol. PAMI–8, No. 4; Regularization of Inverse Visual Problems Involving Discontinuities; pp 413–424.

Lai et al.; IEEE Transactions on Pattern Analysis and Machine Intelligence (1995) vol. 17, No. 11; Deformable Contours: Modeling and Extraction; pp 1084–1090.

Onnasch et al.; Computers in Cardiology, Long Beach, CA, IEEE Computer Society (1975); A Versatile Program for the Documentation and Comparison of Traced Heart Contours; pp 257–262.

Duda et al.; Communications of the ACM (1972) vol. 15, No. 1; Use of the Hough Transformation to Detect Lines and Curves in Pictures; pp 11–15.

Alperin, N. et al.; Automated Analysis of Coronary Lesions From Cineangiograms Using Vessel Tracking and Iterative Deconvolution Techniques; Proceedings. Computers in Cardiology (Cat. No. 89CH2932–2), Jerusalem, Israel; 9/89; pp. 153–156, XP–002156471.

Kitamura, K. et al.; Estimating the 3–D Skeletons and Transverse Areas of Coronary Arteries from Biplane Angiograms; IEEE Transactions on Medical Imaging, vol. 7, No. 3, 9/88; pp. 173–187; XP–002156470.

* cited by examiner

VASCULAR RECONSTRUCTION

FIELD OF THE INVENTION

The invention relates generally to methods and apparatus for reconstructing blood vessels, and particularly to methods and apparatus for three-dimensional reconstructions.

BACKGROUND OF THE INVENTION

The present invention relates to methods for reconstructing blood vessels based on position information acquired from a position sensor contained in a catheter that traverses the vessel.

Blood vessels are visualized today principally by angiography, in which a contrast medium is injected into the bloodstream and the vasculature is imaged using ionizing radiation imaging modalities. Such imaging must be limited however, due to the adverse effects of cumulative radiation on patients. Furthermore, some patients react adversely to the contrast media used in angiography. Accordingly, it would be desirable to have a visualization method that does not depend on ionizing radiation imaging modalities or on the use of contrast agents.

U.S. Pat. No. 5,546,951 and U.S. patent application No. 08/793,371, which are incorporated herein in their entirety by reference, disclose methods for sensing an electrical property of the heart tissue, for example, local activation time, as a function of the precise location within the heart. The data are acquired with one or more catheters that are advanced into the heart, the catheters having electrical and location sensors in their distal tips. Methods of creating a map of the electrical activity of the heart based on these data are disclosed in commonly assigned U.S. patent applications No. 09/122,137 and 09/357,559 filed on Jul. 24, 1998 and Jul. 22, 1999, respectively, which are also incorporated herein in their entirety by reference. As indicated in these applications, location and electrical activity is preferably initially measured on about 10 to about 20 points on the interior surface of the heart. These data points are then generally sufficient to generate a preliminary reconstruction or map of the cardiac surface to a satisfactory quality. The preliminary map is formed by defining an initial, closed 3-dimensional curved surface, preferably of an ellipsoid, in a reconstruction space in the volume of the sample points. The closed curve is roughly adjusted to a shape which resembles a reconstruction of the sample points. Thereafter, a flexible matching stage is repeatedly performed one or more times to bring the closed curve to resemble the shape of the actual volume being reconstructed. While the above-described methods provide satisfactory reconstructions of organs, the algorithms employed therein do not provide accurate reconstructions of blood vessels, particularly when the vessels are convoluted or tortuous in shape.

Reconstruction of blood vessels in images or reconstructions of the heart are beneficial because the blood vessels provide confirmatory landmarks that assist in navigation to specific regions in the heart. Accordingly, it would be desirable to have a method of realistically reconstructing blood vessels that complements existing methods for reconstructing chambers of the heart.

Cardiologists are increasingly attributing atrial fibrillation to defects in the electrical pathways of the heart that originate in the pulmonary vein. Diagnosis and treatment of this condition requires assessing the electrical activity in the pulmonary vein and subsequently ablating defects in or around the vein. Methods for reconstructing the veins with data that may be accumulated with catheters bearing diagnostic or therapeutic components would facilitate the use and outcomes of these procedures.

Certain interventional and diagnostic procedures such as catheterization of the brain are preceded by the generation of images of the vasculature by modalities such as magnetic resonance imaging (MRI). A reconstruction of the vessels effected during the catheterization that could be registered with a previously acquired image would allow the physician to identify the catheter tip location during the procedure with respect to the previously acquired image.

SUMMARY OF THE INVENTION

The present invention is directed to a method for reconstructing the inner surface of a blood vessel using a catheter having a position sensor contained therein. The method of the invention comprises the following steps:

a) advancing the catheter into the vessel;

b) acquiring position information from the sensor at a plurality of points in the vessel;

c) calculating a center-line of the vessel based on said position information; and d) calculating the inner surface of the vessel.

In a preferred embodiment, the method of the invention further comprises the step of displaying the reconstructed vessel surface.

The invention is also directed to apparatus for reconstructing the inner surface of vessels, which comprises:

a) a catheter having a position sensor contained therein;

b) means for acquiring position information from said sensor at a plurality of points in said vessel;

c) means for calculating a centerline of the vessel based on said position information; and d) means for calculating the inner surface of the vessel.

In a preferred embodiment, the apparatus of the invention further comprises means for displaying the vessel reconstruction.

It is an object of the invention to provide a method and apparatus for reconstructing blood vessels without the use of imaging modalities or contrast agents.

It is another object of the invention to provide a method of reconstructing blood vessels that is complementary to methods and apparatus for reconstructing the heart.

It is another object of the invention to provide a method of vessel reconstruction that could provide reconstructions that could be registered with previously acquired images of the vasculature.

These and other objects, features and advantages of the present invention will be more readily apparent for the detailed description set forth below, taken in conjunction with the accompanying drawings.

DETAILED DESCRIPTION OF PREFERRED EMBODIMENTS

The method of the invention for reconstructing the inner surface of a blood vessel using a catheter having a position sensor contained therein comprises the following steps:

a) advancing the catheter into the vessel;

b) acquiring position information from the sensor at a plurality of points in the vessel;

c) calculating a center-line of the vessel based on said position information;

d) calculating the inner surface of the vessel.

The position sensor may, for example, be an electromagnetic, magnetic or acoustic sensor. Electromagnetic sensors are preferred for use in the process of the invention. Exemplary sensors, catheters containing said sensors and systems incorporating said sensors and catheters are described, for example in U.S. Pat. Nos. 4,173,228; 4,697, 595; 4,821,731; 5,042,486; 5,081,993; 5,391,199; 5,558, 091; 5,729,129; 5,752,513; 5,913,820; and 5,954,665; and in PCT Applications WO 96/05768 and WO 97/24983, which are incorporated herein in their entirety by reference.

The position sensor acts as a receiving antenna that receives signals from field generators external to the body. In an alternative embodiment, the position sensor may act as a generator to transmit fields that are received by antennas external to the body.

The position sensor is preferably contained in the catheter at or proximate to the catheter distal tip.

Position information acquired by the position sensor contained in the catheter can be used to provide a reconstruction or a map of the physical dimensions of the vessel or vasculature. If additional functional components are contained in the catheter, condition information describing a condition of the blood vessel, may be collected together with position information. As used herein, the term "condition" refers to either a scalar or a vector quantity, and may comprise, for example, an electrical property, a temperature, a pressure, a pH, a measure of local vessel movement or any other condition or combination thereof. For example, the use of a catheter having an electrophysiology electrode in addition to a position sensor permits the simultaneous collection of position and electrical condition information in the vessel. Exemplary electrical condition information that may be collected includes but is not limited to voltage, impedance, conduction velocity and local activation time (LAT). The combined position and condition information may be used to generate a map of the condition information as a function of the spatial coordinates within the vessel.

The catheters used in the method of the invention may also contain other functional components for effecting therapeutic functions within the body, such as electrodes for selectively ablating tissue within the vessel or other organ within the body.

Figure 1:
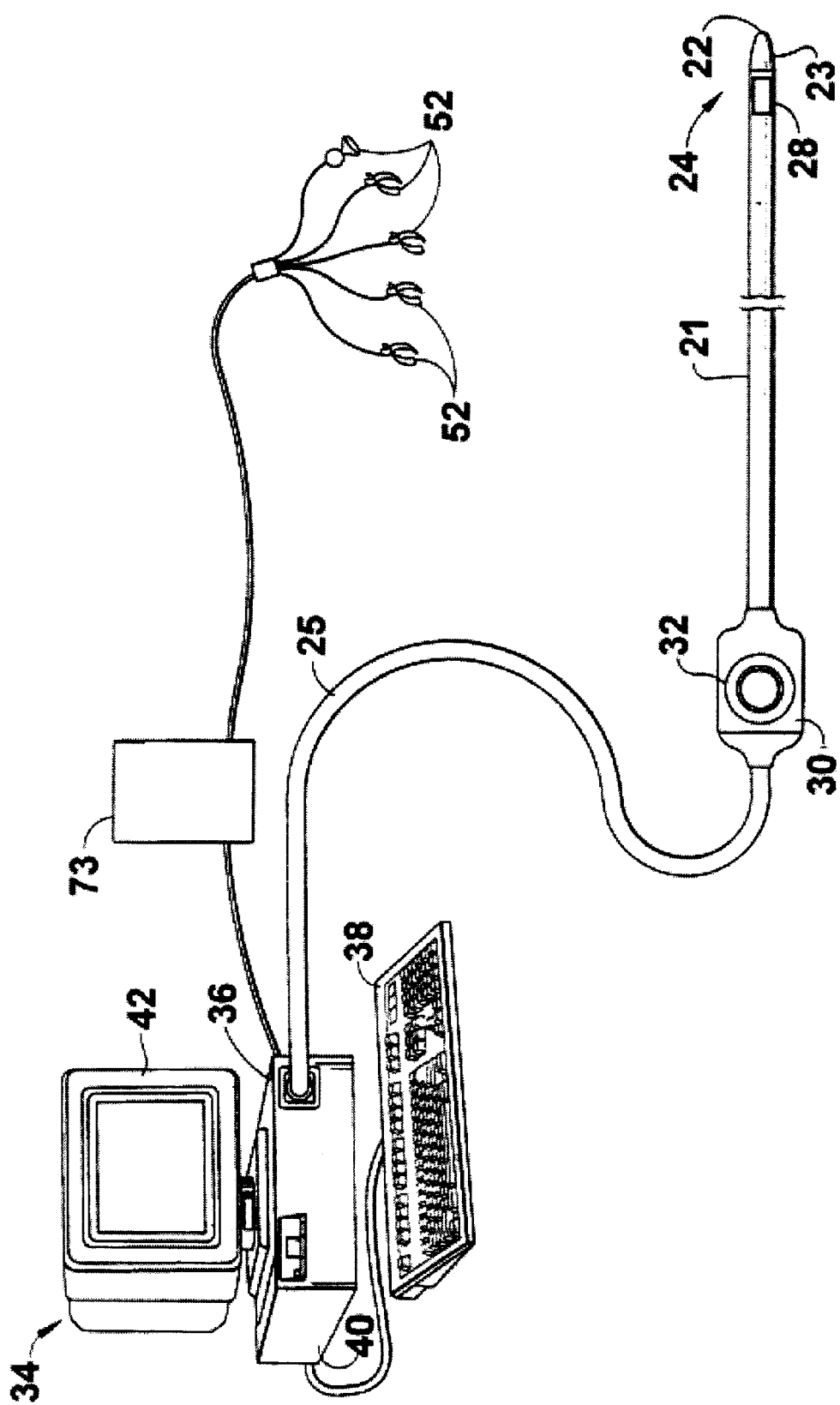
FIG. 1 is a schematic drawing of apparatus used to practice the method of the invention.

FIG. 1 shows a preferred apparatus for carrying out the method of the invention. The apparatus comprises catheter 21 for insertion into the human body. Distal end 24 of catheter 21 includes a sensor 28 that generates signals used to determine the position, and, optionally, the orientation of the catheter within the body. Sensor 28 is preferably an electromagnetic sensor comprising a plurality of coils as described in PCT application WO96/05768, which is incorporated herein in its entirety by reference. This sensor enables continuous generation of up to six dimensions of position and orientation information with respect to externally applied magnetic fields. Alternatively, sensor 28 may comprise only a single sensing coil as described in U.S. Pat. No. 5,913,820. Sensor 28 may comprise other position and/or coordinate sensors as described in U.S. Pat. No. 5,391,199, U.S. Pat. No. 5,443,489 and PCT application WO94/04938 which are incorporated herein by reference. Further, tip 22 may be coated with an opaque marking material to visualize the tip under an imaging apparatus such as a fluoroscope.

Distal end 24 of catheter 21 optionally includes a functional portion 23 for performing diagnostic and/or therapeutic functions, adjacent to distal tip 22. Functional portion 23 preferably comprises electrodes or sensors for performing electrophysiological measurements, as described, for example, in U.S. Pat. No. 5,391,199 or in PCT application WO97/24983, which are incorporated herein by reference. Alternatively or additionally, functional portion 23 may include other diagnostic apparatus for acquiring parameter values at points within the body. Functional portion 23 may also include therapeutic apparatus as known in the art.

Sensor 28 is preferably adjacent to and in a fixed relationship relative to functional portion 23 and to tip 22 of catheter 21.

Catheter 21 preferably includes a handle 30, having controls 32 which are used to steer distal end 24 of catheter 21 in a desired direction. Catheter 21 preferably comprises a steering mechanism in distal end 24 as is known in the art to facilitate repositioning of tip 22.

Catheter 21 is coupled via an extension cable 25 to a console 34 which enables the user to observe and regulate the function of catheter 21. Console 34 preferably includes a computer 36, keyboard 38, signal processing circuitry 40, which are typically inside computer 36, and display 42. Signal processing circuits 40 typically receive, amplify, filter and digitize signals from catheter 21, including signals from sensor 28 and functional portion 23, whereupon these digitized signals are used by computer 36 to compute the position and/or orientation of catheter tip 22 and to record condition information measured from functional portion 23. Alternatively, appropriate circuitry may be associated with catheter 21 itself so that circuits 40 receive signals that are already amplified, filtered and/or digitized. Preferably, computer 36 includes a memory for storing position and condition information. Computer 36 also comprises means for capturing images from an imaging modality either using a video or a DICOM protocol interface. Computer 36 preferably further comprises dedicated graphics hardware for rapidly calculating the vessel reconstructions and for displaying them on display 42. Preferably, the computer is equipped to receive body surface ECG signals from ECG monitor 73 which is connected to a plurality of ECG body surface leads 52. Alternatively, ECG monitoring may also be conducted directly by circuits 40. Since blood vessels undergo movement as a function of the cardiac cycle, the use of the body surface ECG permits the gating of the position information and the resultant reconstruction to a single point in the cardiac cycle.

An algorithm is used in the reconstruction of the vessel from the position information acquired at a plurality of acquisition points by the position sensor. The input to the algorithm is a series of three-dimensional sensor locations $P_1, P_2, \ldots, P_n$, that are acquired within the vessel such that $P_i=(x_i, y_i, z_i)$ wherein $x_i$, $y_i$ and $z_i$ are the particular coordinates of the $i^{th}$ acquisition point.

Figure 2B:
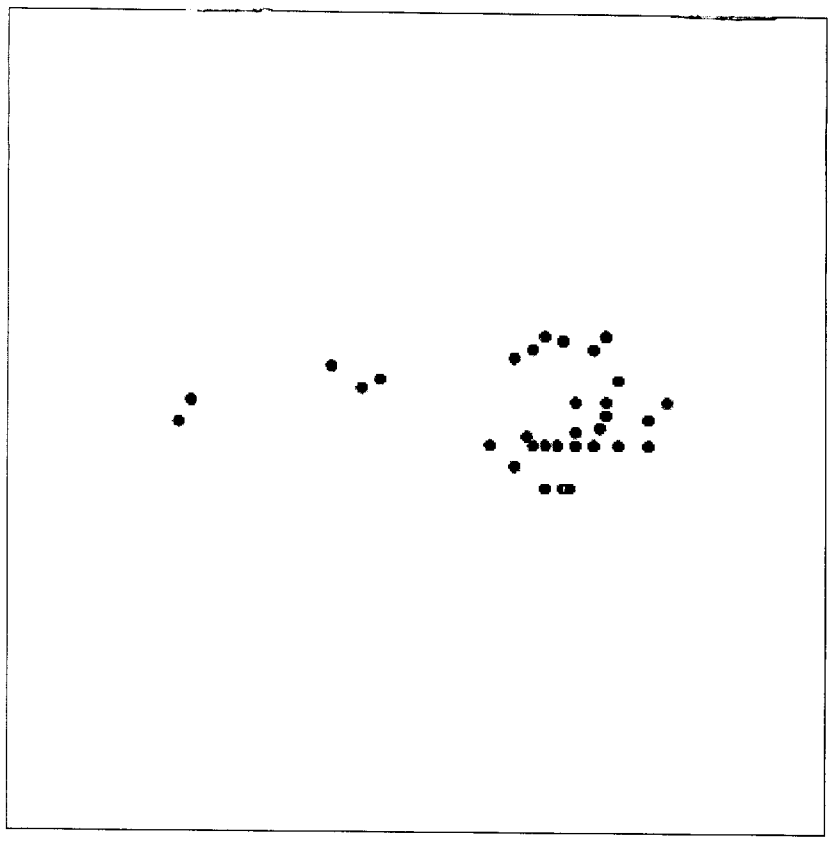
FIG. 2B shows the projection of the positions of FIG. 2A rotated by 90°.
Figure 2A:
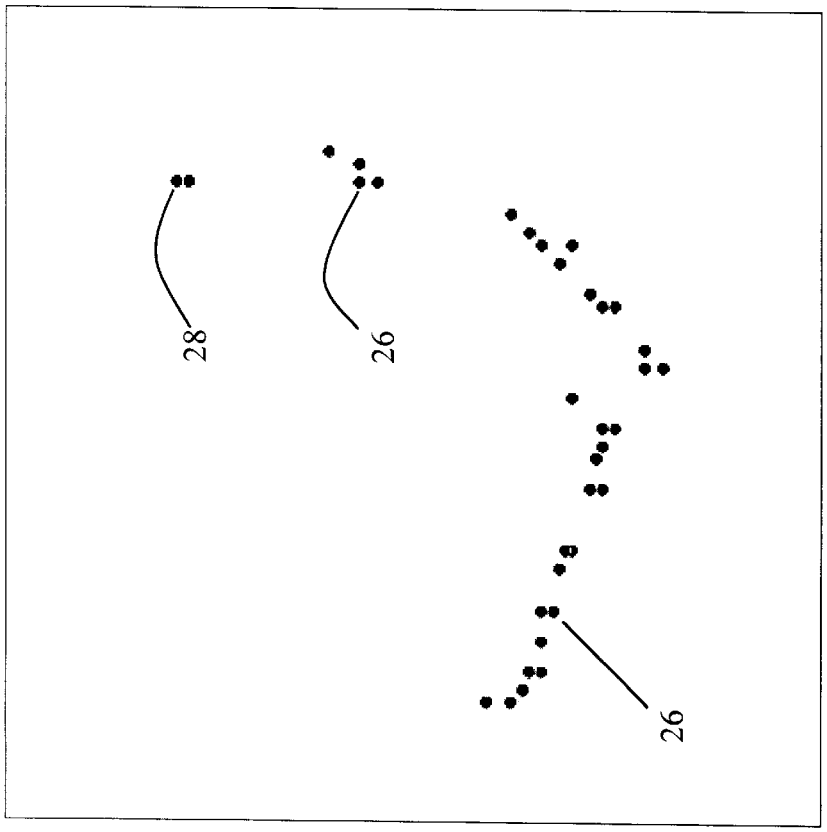
FIG. 2A shows a two-dimensional projection of positions that are acquired in a blood vessel using a catheter having a position sensor contained therein.

FIG. 2A shows a two dimensional projection of the positions of points 26 at which position information is acquired using the above-described catheter and sensor. FIG. 2B shows the plot of the acquisition points of FIG. 2A rotated 90° about the vertical axis of FIG. 2A.

The algorithm used in the method of the invention approximates the inner surface of the vessel such that cross-sections of the vessel perpendicular to the vessel centerline are circular or nearly circular in shape. One of ordinary skill in the art will appreciate that the method of the invention may be applied to generate reconstructions having other cross-sectional shapes, such as an elliptical or polygonal shape, for example.

The vessel is reconstructed in two steps: first, the centerline of the vessel is calculated. Then the vessel wall of appropriate radius or cross-section is calculated around the centerline.

CALCULATION OF THE VESSEL CENTERLINE

We use $d_{ij}=\|P_i-P_j\|$, the distance between sample point $P_i$ and $P_j$, to find an extreme point, $P_m$, (28 in FIG. 2A) which is the sample point that is the most remote from all other sample points, i.e.

$$m = \underset{i}{\operatorname{maxarg}} \sum_j d_{ij}^2.$$

In other words, for each point, we calculate the distance from that point to all other points. The extreme point, $P_m$, is that point having the longest distance from itself to the other points. The distance between the points from which to base the selection of $P_m$ is assessed, as in the above equation, as the sum of squares of the distances between points.

We denote the distance between a sample point, $P_i$, and the extreme point, $P_m$, by $d_i$, i.e., $d_i=d_{mi}$.

Let d =max $d_i$, the maximum distance between the extreme point and any of the other points. We may then define $t_i$ as:

$$t_i = \frac{d_i}{d} \in [0, 1].$$

The vessel centerline is a one-dimensional line embedded in three-dimensional space. The centerline represents the locus of all geometric centers of all possible cross-sections of the vessel.

We seek a parametric representation of the vessel centerline that is of the form:

$$F(t)=(X(t), Y(t), Z(t)) \; t \in [0,1]$$

wherein $X(t)$, $Y(t)$ and $Z(t)$ are functions of t that represent the coordinates of the centerline.

Each location $P_i$ has a corresponding point $F(t_i)$, the point on the centerline closest to $P_i$. The representation of the centerline $F(t)$ preferably minimizes the distance between the centerline and the sample points in a least squares sense, i.e., $\Sigma \|(t_i)-P_i\|^2$ is minimal over the function space.

The following series of polynomials of degree k are used for calculating the centerline representation:

$$X(t) = \sum_{j=0}^{k} a_j t^j$$

$$Y(t) = \sum_{j=0}^{k} b_j t^j$$

$$Z(t) = \sum_{j=0}^{k} c_j t^j.$$

We wish to use a polynomial of high enough degree to be able to fit the data but of low enough degree to avoid over-fitting the data. In practice, a third degree polynomial fit, i.e., in which k=3, is preferred.

For each of the above polynomial equations (one for each coordinate dimension), we solve a system of linear equations whose unknowns are the coefficients $a_j$, $b_j$ and $c_j$=0, . . . ,k). The system of equations equates the polynomials $X(t)$, $Y(t)$ and $Z(t)$ with the respective coordinates of each of the acquired data points according to the following equations:

$$X(t_i)=x_i, i=1, \ldots, n$$

$$Y(t_i)=y_i, i=1, \ldots, n$$

$$Z(t_i)=z_i, i=1, \ldots, n$$

Singular value decomposition is a robust, preferred method for solving these systems of equations (see for example, "Numerical Recipes in C: The Art of Scientific Computing", William T. Vetterling (Editor), Saul A. Teukolsky, William H. Press (Editor), and Brian P. Flannery, Cambridge University Press, pp 59–70, 1997).

Figure 3B:
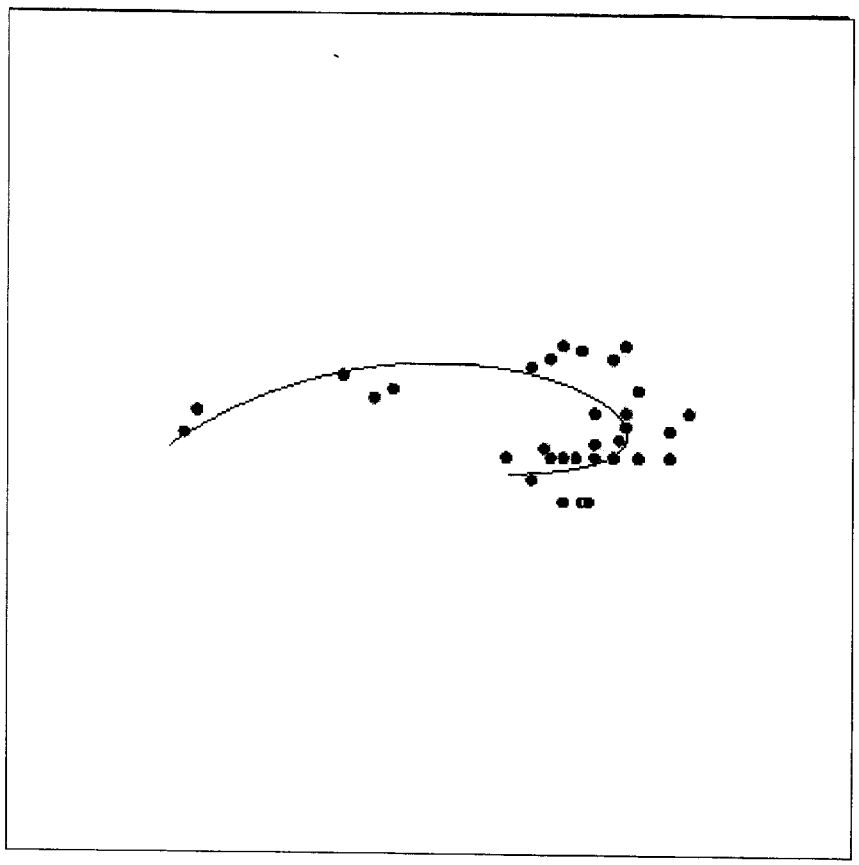
FIG. 3B shows the projection of the positions and centerline of FIG. 3A rotated by 90°.
Figure 3A:
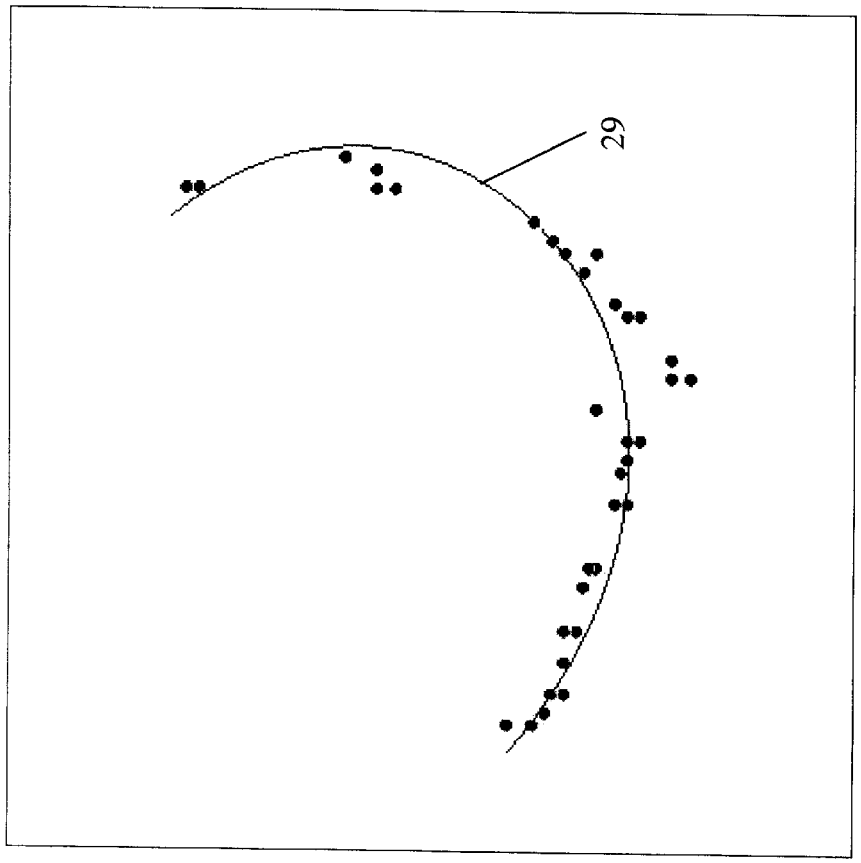
FIG. 3A shows the projection of the positions of FIG. 2A together with a computed vessel centerline.

FIG. 3A shows a two-dimensional projection of the original acquisition points as well as the computed centerline 29. FIG. 3B shows the points and centerline of FIG. 3A rotated by 90°.

CALCULATION OF THE VESSEL WALL ABOUT THE CENTERLINE

As indicated above, the algorithm used in the method of the invention approximates the inner surface of the vessel wall such that cross-sections of the vessel perpendicular to the vessel centerline are circular or polygonal in shape.

Thus, the reconstruction models the vessel as a whole as being tubular in shape.

A three-dimensional reconstruction about the centerline may be performed to generate a tube of either fixed or variable radius (fixed or variable cross-section).

Reconstruction of the vessel as a tube is performed by calculating circular or polygonal slices or cross-sections around, and preferably perpendicular to the centerline, and connecting the slices together to form a tube.

The tangent to the centerline may be expressed by the following series of equations:

$$D(t) = \frac{d}{dt}F(t) = \left(\frac{d}{dt}X(t), \frac{d}{dt}Y(t), \frac{d}{dt}Z(t)\right)$$

where $$\frac{d}{dt}X(t) = \sum_{j=1}^{k} a_j j t^{j-1}$$

$$\frac{d}{dt}Y(t) = \sum_{j=1}^{k} b_j j t^{j-1}$$

$$\frac{d}{dt}Z(t) = \sum_{j=1}^{k} c_j j t^{j-1}$$

Denoting $$\eta(V) = \frac{V}{\|V\|},$$

one of the unit vectors normal to the centerline may be expressed as:

$$N_0(t) = \eta\left(-\frac{d}{dt}Y(t), \frac{d}{dt}X(t), 0\right)$$

Figure 4B:
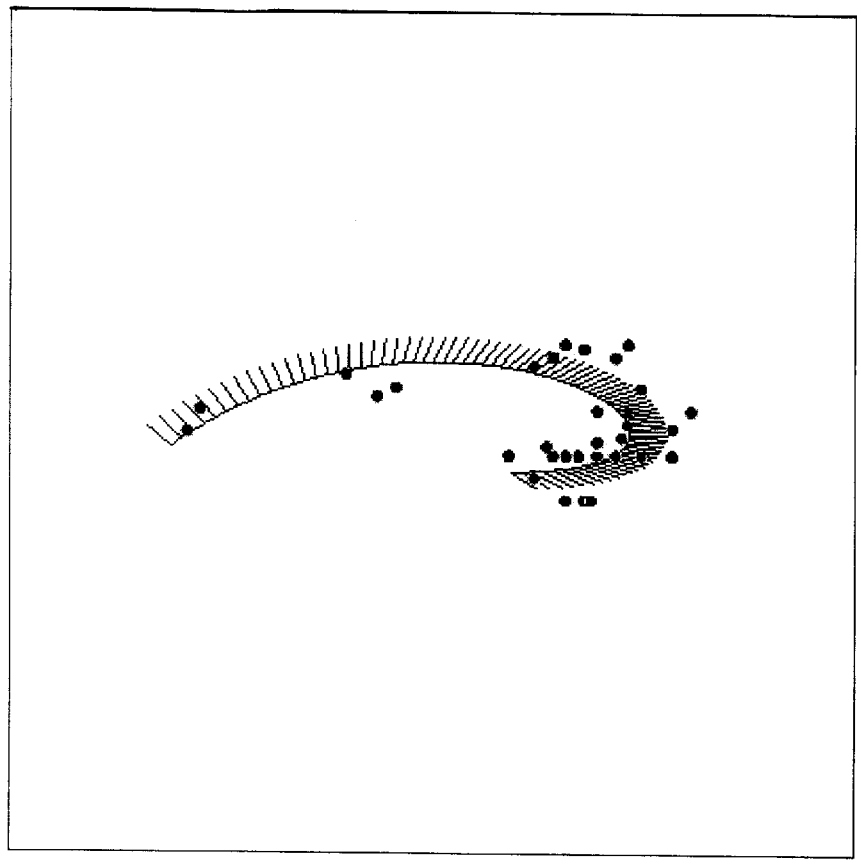
FIG. 4B shows a projection of the points, centerline and vectors of FIG. 4A rotated 90° around the vertical axis.
Figure 4A:
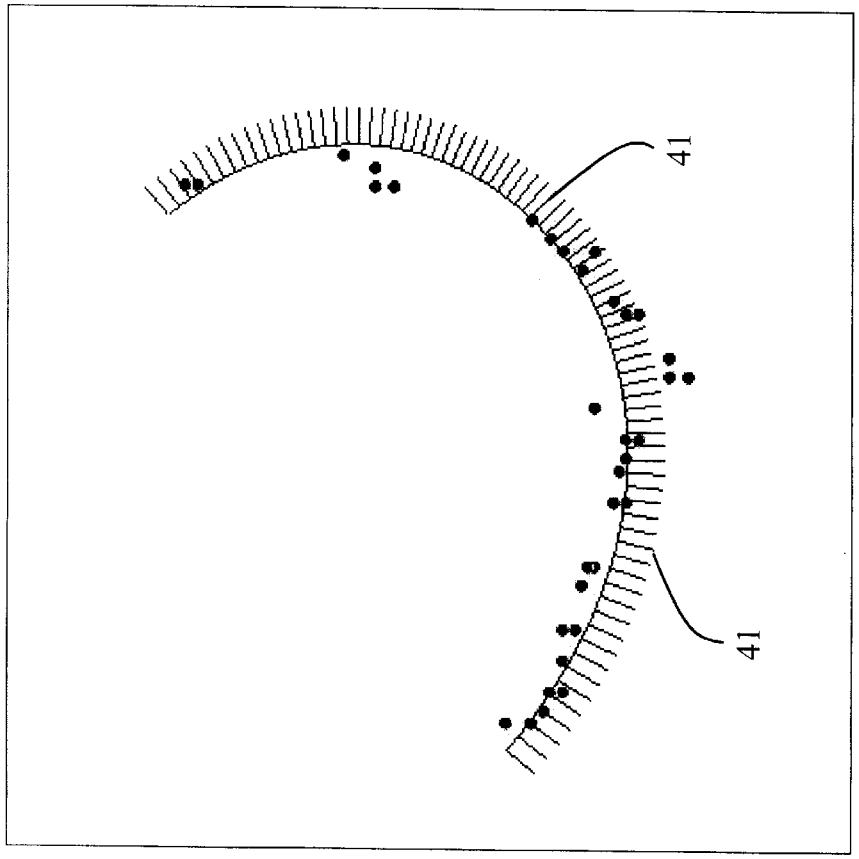
FIG. 4A shows a projection of the points and centerline of FIG. 3A with normal vectors drawn at increments perpendicular to the centerline.

FIG. 4A shows the points and centerline of FIG. 3A with normal vectors 41 drawn at increments perpendicular to the centerline. FIG. 4B shows the points, centerline and vectors of FIG. 4A rotated 90° around the vertical axis.

Another unit vector normal to the centerline that is perpendicular to the previous vector may be expressed by the equation:

$$N_1(t) = D(t) \times N_0(t)$$

Two additional unit vectors are $-N_0(t)$ and $-N_1(t)$. Thus, a set of four vectors $N^0(t)$ normal to centerline $F(t)$ are ordered counterclockwise in 90° increments about the centerline as follows:

$$N^0(t) = (N_0(t), N_1(t), -N_0(t), -N_1(t))$$

$N^0(t)$ is a very crude sampling of the vectors emanating from the centerline and projecting onto a circle around the centerline $F(t)$. Given a set of vectors $N^i(t)$ that sample the circle around the centerline, additional vectors are in the direction of the sum of previously calculated vectors. Thus, given a set of four vectors, $N^0(t)$, the set may be expanded to a new set, $N^1(t)$ containing 8 vectors as shown below:

$$N_{2j}^{i+1}(t) = N_j^i(t) \; N_{2j+1}^{i+1}(t) = \eta(N_j^i(t) + N_{j+1}^i(t))$$

Another set of vectors, $N^2(t)$, containing 16 vectors, may be similarly generated from $N^1(t)$, and so on.

Finally, let r be the radius of the tube about any point on the centerline. For a tube of fixed radius, a point on the surface of the tube around centerline $F(t)$ which corresponds to the vector $N_i(t)$ is $$S_i(t) = F(t) + r \, N_i(t)$$

The radius r of the tube may be chosen based on the position information of the points and their distances from the centerline. For example, radius r may be chosen as the average or the median of the distances of the points from the centerline. Alternatively, the reconstruction may be performed using a value of r selected by the user that may be typical of the dimensions of the vessel under reconstruction.

Figure 5B:
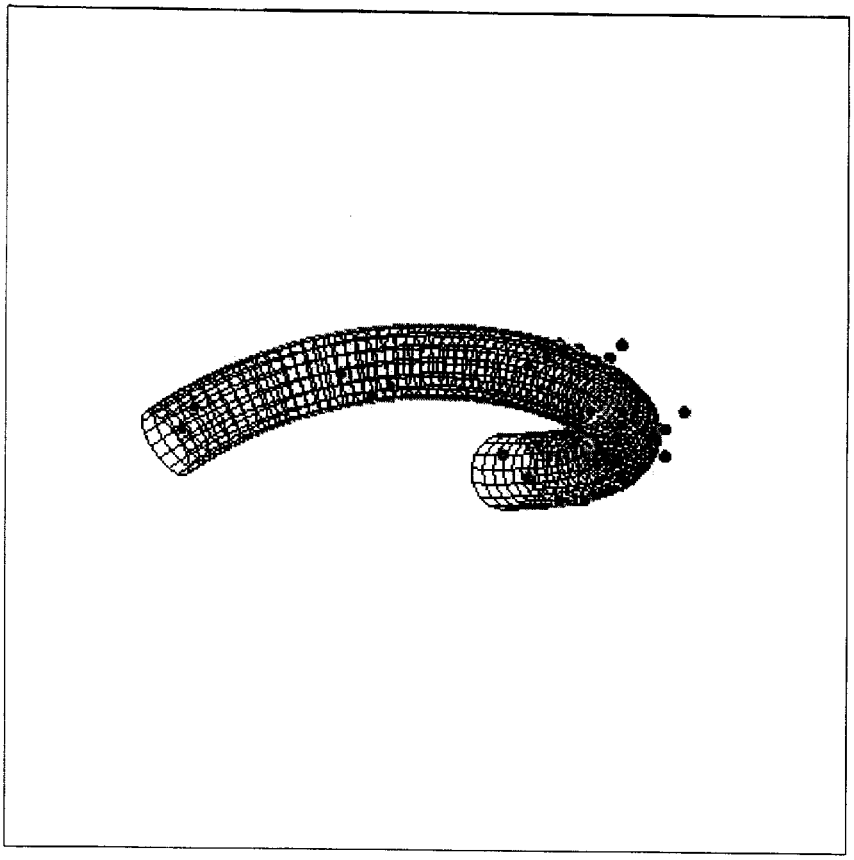
FIG. 5B shows the wire frame reconstruction of vessel of FIG. 5A rotated by 90°.
Figure 5A:
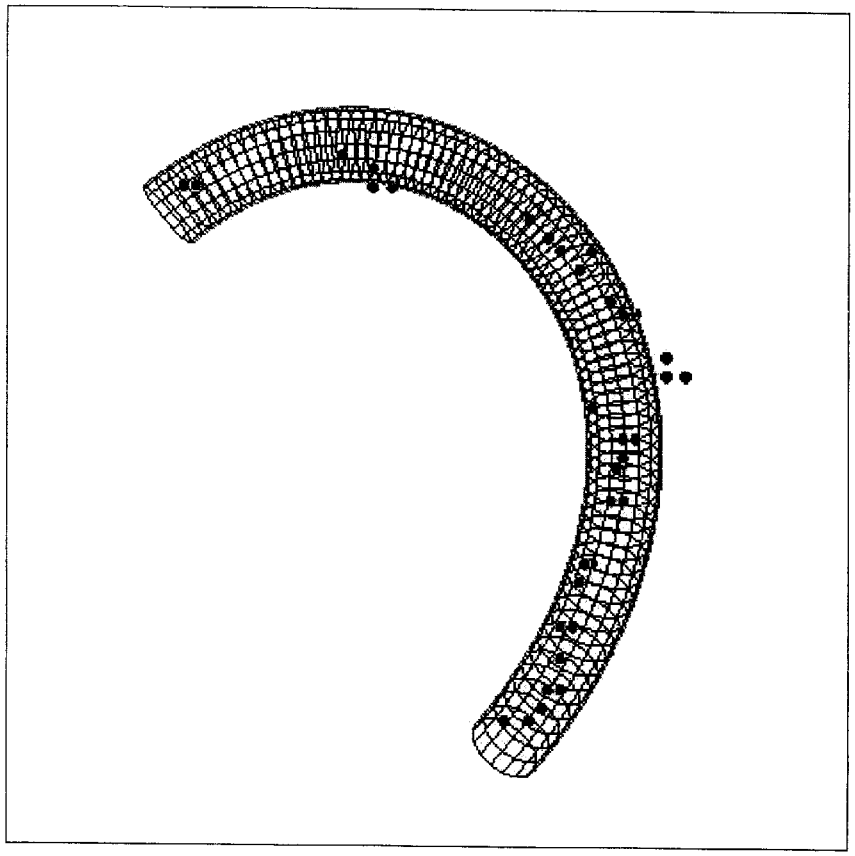
FIG. 5A shows a wire-frame reconstruction of the vessel positions depicted in FIG. 2A.
Figure 5C:
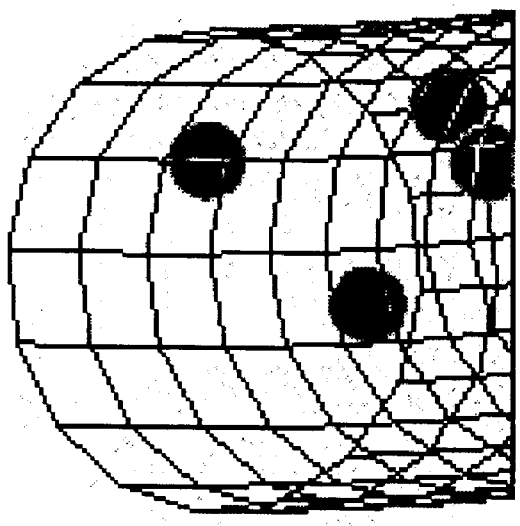
FIG. 5C shows an expanded view of a portion of the wireframe reconstruction of FIG. 5B.

A wire-frame reconstruction of the tubular-shaped vessel is built from small rectangular patches whose vertices are $S_i(t)$, $S_i(t+\Delta)$, $S_{i+1}$, $(t+\Delta)$, $S_{i+}$, $(t)$, i.e., points corresponding to two contiguous vectors in a slice, each of said points connected to corresponding points on the next adjacent slice or cross-section of the tube. FIG. 5A shows the wire frame reconstruction of the points, centerline and first vectors of FIG. 4A. FIG. 5B shows the wire-frame reconstruction of FIG. 5A rotated 90° around its vertical axis. FIG. 5C shows a greatly magnified view of a portion of the wire frame reconstruction of FIG. 5B. In the reconstruction as seen in FIG. 5C, each slice of the reconstruction is composed of a 16-sided polygon. It will be appreciated that as the number of sides in the polygon is increased, the vessel reconstruction will appear more circular in cross-section. Each vertex of the polygon represents the radius (not shown) emanating from the centerline (not shown) in the direction of one of the aforesaid unit vectors. The sides of the polygon are made by connecting contiguous vertices within a slice with straight lines. The squares connecting the slices are made by connecting the corresponding vertices on adjacent slices with straight lines.

Figure 6B:
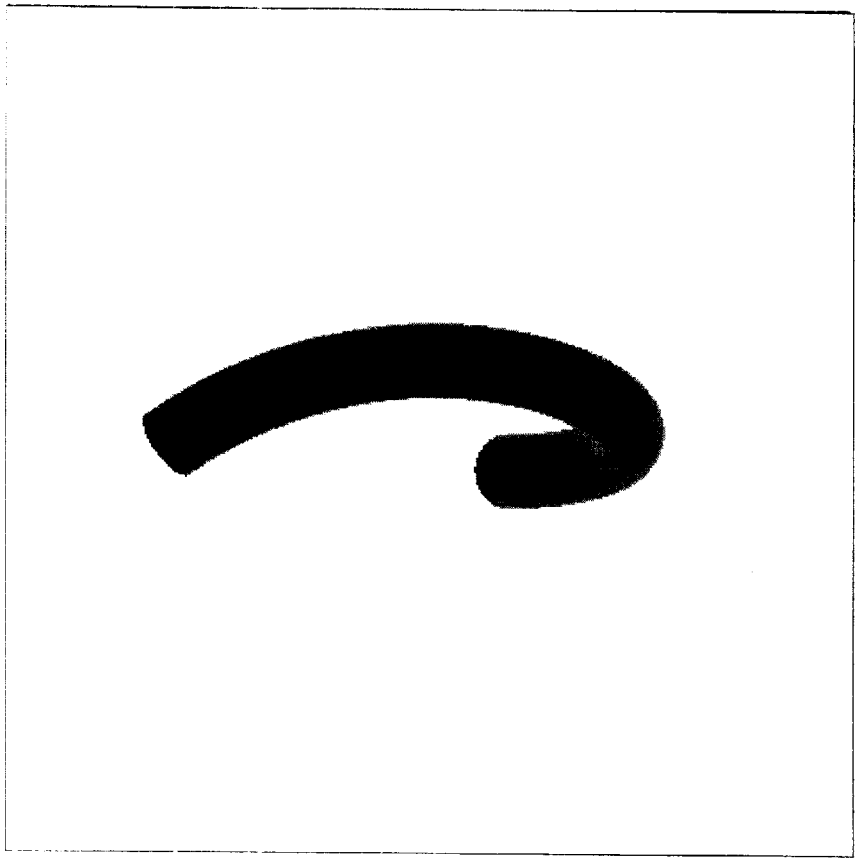
FIG. 6B shows a shaded reconstruction of the vessel of FIG. 6A rotated by 90°.
Figure 6A:
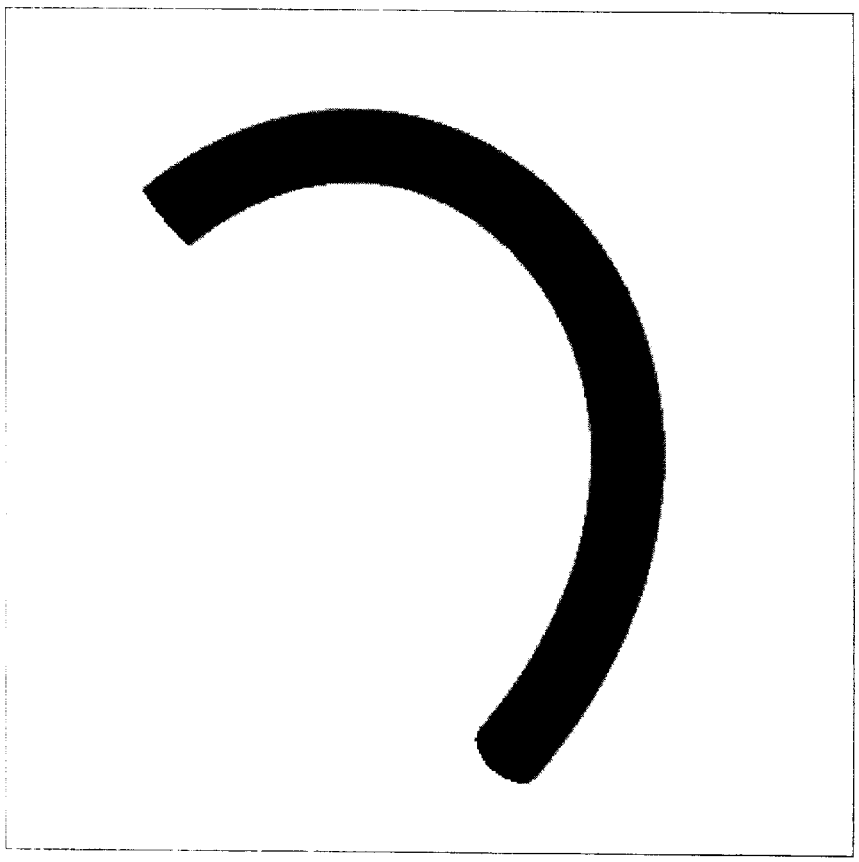
FIG. 6A shows a shaded reconstruction of the vessel positions depicted in FIG. 2A.

The reconstruction is completed by shading the squares making up the wire-frame reconstruction. FIG. 6A and FIG. 6B show the shaded reconstructions of FIG. 5A and FIG. 5B, respectively. Using standard graphic methods known in the art (see for example "OpenGL(r) 1.2 Programming Guide, Third Edition: The Official Guide to Learning OpenGL, Version 1.2", Mason Woo, et. al., Addison-Wesley Publishing Company, New York, N.Y., 1999), the individual rectangles comprising the wire-frame reconstruction may be shaded using a gray scale or a color scale to lend perspective to the otherwise flat two-dimensional representation of the three dimensional vessel structure. Alternatively, if position information is collected together with condition information using a catheter having both a position and condition sensor, the wire frame reconstruction may be shaded or colored such that the colors or shades of the individual squares represent different values of the condition information as a function of vessel coordinates.

As indicated hereinabove, the method of the invention may be used to provide a reconstruction of the vessel having either a fixed or a variable cross-section. Reconstruction of a tube with a variable radius or cross-section requires a modified slice formula:

$$S_i(t) = F(t) + r(t) N_i(t)$$

wherein r(t), the slice radius around centerline $F(t)$, is itself a function of (t).

As indicated above, each sample point, $P_i$, has a corresponding point on the centerline, $F(t_i)$, to which it is closest. The distance from $P_i$ to its corresponding point $F(t_i)$ on the centerline, $\|P_i - F(t_i)\|$, is an indication of the vessel radius at F($t_i$). The radius of a slice may be determined by averaging the distances between sample points and their corresponding centerline points in vicinity of the slice center. For each slice, points closer to the slice may be accorded greater weight in the computation of the average. In other words, the radius of a slice may be computed as a weighted average of the distance between the points to the centerline, with greater weight being accorded to points closer to the slice.

Figure 8:
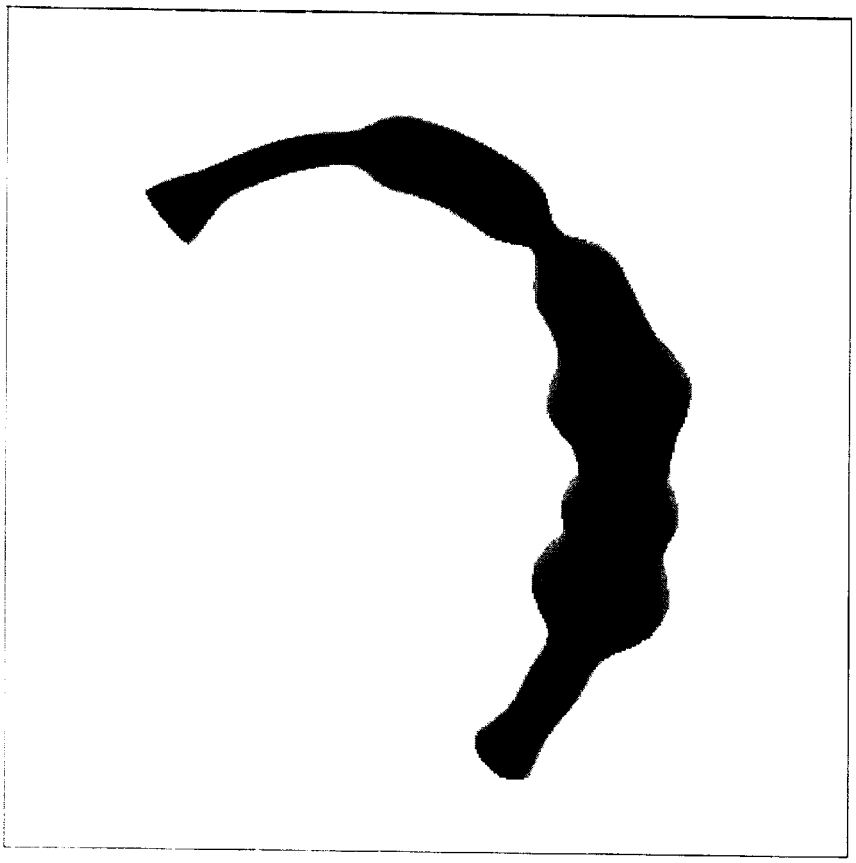
FIG. 8 shows a shaded reconstruction of the vessel positions of FIG. 2A in which the vessel was reconstructed with a variable radius algorithm.
Figure 7:
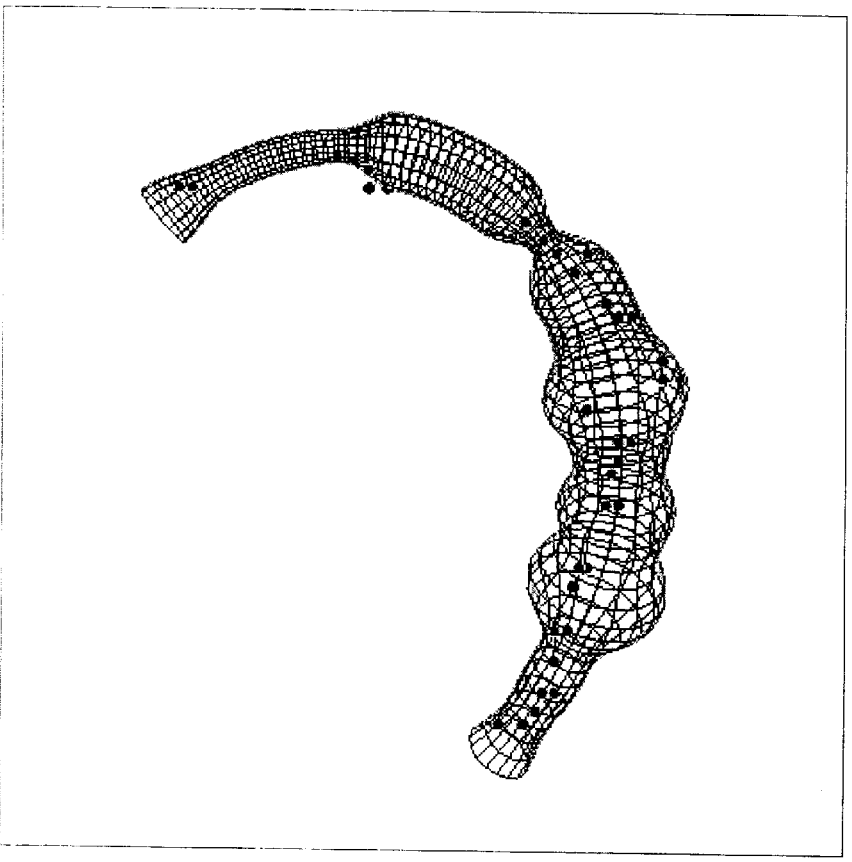
FIG. 7 shows a wire frame reconstruction of the vessel positions of FIG. 2A in which the vessel was reconstructed with a variable radius algorithm.

FIG. 7 and FIG. 8 show the wire-frame and shaded reconstructions, respectively, of the position information of FIG. 2A using the above-described variable radius reconstruction algorithm.

The decision to reconstruct the vessel with a fixed or variable radius depends on a number of factors. A high quality reconstruction of a tube with variable radius requires more data points taken around the vessel cross-section. This requirement translates into longer procedure time to acquire the points. Alternatively, a fixed radius tube may be reconstructed from fewer data points around the vessel cross-section, which may be acquired, for example by merely traversing the catheter through the vessel. A fixed radius reconstruction would be silent on variations in cross-section of the vessel, but would, nevertheless, be expected to accurately portray the three-dimensional vessel shape.

Figure 9B:
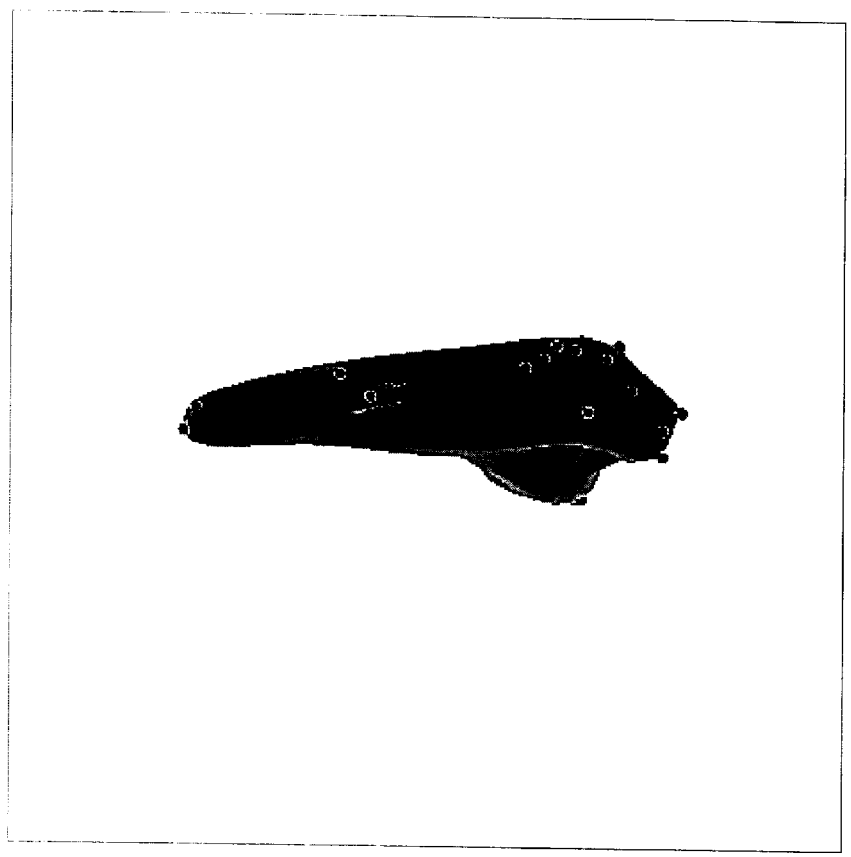
FIG. 9B shows the reconstruction of FIG. 9A rotated by 90°.
Figure 9A:
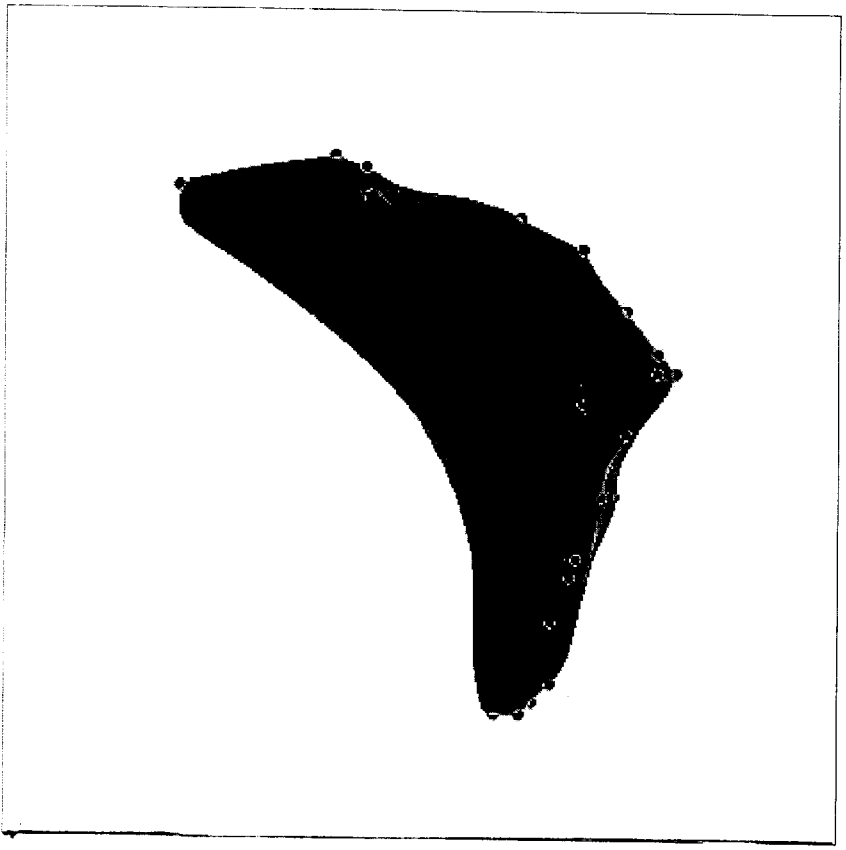
FIG. 9A shows a reconstruction of the points of FIG. 2A and FIG. 2B using an algorithm designed for reconstruction of an organ such as the heart.

As previously indicated, copending commonly assigned applications 09/122,137 and 09/357,559 disclose methods of mapping the electrical activity of the heart. The reconstruction disclosed in these applications is effected by generating a preliminary map by defining an initial, closed 3-dimensional curved surface, preferably of an ellipsoid, in a reconstruction space in the volume of the sample points. The closed curve is roughly adjusted to a shape which resembles a reconstruction of the sample points. Thereafter, a flexible matching stage is repeatedly performed one or more times to bring the closed curve to resemble the shape of the actual volume being reconstructed. The data of FIG. 2A and FIG. 2B were reconstructed using the algorithm of these copending applications, and shaded reconstructions of the data using those methods are shown in FIG. 9A and FIG. 9B. It will be appreciated that the method of the invention successfully in reconstructs vessels more realistically than the above-disclosed methods designed for heart reconstructions.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A method of reconstructing the inner surface of a blood vessel using a catheter having a position sensor contained therein, said sensor generating signals responsive to the position and/or the orientation of the catheter within the body, said method comprising:
    a) advancing the catheter into the vessel;
    b) acquiring signals from the sensor and calculating position information from said acquired signals at a plurality of acquisition points in the vessel;
    c) calculating a centerline of the vessel based on said position information;
    d) calculating the inner surface of the vessel.

2. The method of claim 1 wherein the centerline is described as a parametric function.

3. The method of claim 2 wherein the parametric function is of a polynomial form.

4. The method of claim 1 wherein the distances between acquisition points and respective points on the centerline closest to said acquisition points are minimized.

5. The method of claim 4 wherein said distances are minimized in a least squares sense.

6. The method of claim 1 wherein said inner vessel surface is reconstructed in approximately circular cross-section.

7. The method of claim 1 wherein said reconstruction comprises calculating slices of the vessel about said centerline.

8. The method of claim 7 wherein said slices are perpendicular to said centerline.

9. The method of claim 8 wherein said slices perpendicular to said centerline have a fixed cross-section.

10. The method of claim 8 wherein said slices perpendicular to said centerline have a variable cross-section.

11. The method of claim 1 wherein the distance from each point on the reconstruction to the centerline is a function of the distances of the acquisition points to the centerline.

12. The method of claim 11 wherein the distance from each point on the reconstruction to the centerline is the average distance of the acquisition points to the centerline.

13. The method of claim 11 wherein the distance from each point on the reconstruction to the centerline is the median distance of the acquisition points to the centerline.

14. The method of claim 11 wherein said function is a weighted average of the distances of the acquisition points to the centerline.

15. The method of claim 14 wherein said weighted average accords greater weight to proximate acquisition points.

16. The method of claim 11 wherein said distance is user selected.

17. The method of claim 1 which further comprises acquiring condition information at said acquisition points.

18. The method of claim 17 wherein said reconstruction is color-coded to depict values of said condition information.

19. The method of claim 17 wherein values of condition information on the vessel surface intermediate said acquisition points are interpolated.

20. The method of claim 1 which further comprises the step of displaying the reconstructed vessel surface.

21. The method of claim 1 wherein said position information is obtained by traversing the catheter in the vessel.

22. The method of claim 1 wherein said position information is obtained by sampling points on the vessel wall around the vessel cross-section.

23. The method of claim 1 wherein said position sensor is an electromagnetic sensor.

24. Apparatus for reconstructing the inner surface of a blood vessel comprising:
    a) catheter having a position sensor contained therein, said sensor generating signals responsive to the position and/or the orientation of the catheter within the body;
    b) means for acquiring signals from said sensor at a plurality of points in said vessel and for calculating position information from said acquired signals;
    c) means for calculating a centerline of the vessel based on said position information; and
    d) means for calculating the inner surface of the vessel.

25. The apparatus of claim 24 which further comprises means for displaying the reconstruction.

26. The apparatus of claim 24 wherein said sensor is an electromagnetic sensor.

* * * * *